United States Patent
Stoker et al.

(10) Patent No.: US 10,180,402 B2
(45) Date of Patent: Jan. 15, 2019

(54) METHOD AND APPARATUS FOR CONDUCTING AUTOMATED INTEGRATED CIRCUIT ANALYSIS

(71) Applicant: SRI International, Menlo Park, NJ (US)

(72) Inventors: David S. Stoker, Belmont, CA (US); Erik Frank Matlin, Los Gatos, CA (US); Motilal Agrawal, San Carlos, CA (US); James R. Potthast, San Jose, CA (US); Neil William Troy, Santa Clara, CA (US)

(73) Assignee: SRI International, Menlo Park, CA (US)

( * ) Notice: Subject to any disclaimer, the term of this patent is extended or adjusted under 35 U.S.C. 154(b) by 610 days.

(21) Appl. No.: 14/066,111

(22) Filed: Oct. 29, 2013

(65) Prior Publication Data

US 2014/0172345 A1    Jun. 19, 2014

Related U.S. Application Data

(60) Provisional application No. 61/772,712, filed on Mar. 5, 2013, provisional application No. 61/737,516, filed on Dec. 14, 2012.

(51) Int. Cl.
*G01N 21/95* (2006.01)
*G06F 17/50* (2006.01)
*G01R 31/311* (2006.01)

(52) U.S. Cl.
CPC ........... *G01N 21/95* (2013.01); *G01R 31/311* (2013.01); *G06F 17/5081* (2013.01)

(58) Field of Classification Search
CPC ......... G01N 27/90046; G01N 21/3581; G01N 29/22; G06K 9/00476; G06K 9/3233;
(Continued)

(56) References Cited

U.S. PATENT DOCUMENTS 5,430,305 A  *  7/1995 Cole, Jr. .............. G01R 31/311
                                                    250/559.07
5,479,252 A     12/1995 Worster et al.
(Continued)

FOREIGN PATENT DOCUMENTS

JP     2006513560     4/2006
JP     2006319193     11/2006
(Continued)

OTHER PUBLICATIONS

Yee et al., "Laser voltage probe (LVP): a novel optical probing technology for flip-chip packaged microprocessors." Physical and Failure Analysis of Integrated Circuits, 1999. Proceedings of the 1999 7th International Symposium on the. IEEE, pp. 15-20, 1999.
(Continued)

*Primary Examiner* — Regis Betsch
*Assistant Examiner* — Kaleria Knox
(74) *Attorney, Agent, or Firm* — Moser Taboada

(57) ABSTRACT

A method and apparatus for scanning an integrated circuit comprising a plurality of time-synchronized laser microscopes, each of which is configured to scan the same field of view of an integrated circuit under test that generates a plurality of images of the integrated circuit under test, a data processor, coupled to the laser scanning microscope, for processing the plurality of images, comprising, a netlist extractor (NE) that produces one or more netlists defining structure of the integrated circuit under test.

25 Claims, 11 Drawing Sheets

(58) Field of Classification Search
CPC ..... G01S 15/584; G01S 13/36; G09G 3/3466; G01R 31/308; G01R 31/311; H01L 22/20
USPC ....... 324/228, 123, 754.23, 754.27; 382/145, 382/284; 600/453, 476; 342/123; 372/31; 356/519, 432; 257/E21.525; 250/559.07
See application file for complete search history.

(56) References Cited

U.S. PATENT DOCUMENTS

| | | | |
|---|---|---|---|
| 5,905,577 A | 5/1999 | Wilsher et al. | |
| 6,236,746 B1* | 5/2001 | Chamberlain | G06K 9/00476 382/145 |
| 6,381,019 B1* | 4/2002 | Maris | G01N 29/22 356/432 |
| 6,496,261 B1 | 12/2002 | Wilsher et al. | |
| 6,536,018 B1 | 3/2003 | Chisholm et al. | |
| 6,549,022 B1* | 4/2003 | Cole, Jr. | G01R 31/308 324/754.23 |
| 6,608,854 B1* | 8/2003 | Watanabe | H01S 5/0608 372/31 |
| 6,894,518 B1* | 5/2005 | Bruce | G01R 31/311 324/754.27 |
| 7,126,699 B1 | 10/2006 | Wihl et al. | |
| 7,250,757 B1* | 7/2007 | Tiernan | G01N 27/9046 324/228 |
| 7,310,585 B2* | 12/2007 | Brodsky | H01L 22/20 257/E21.525 |
| 7,450,245 B2 | 11/2008 | Woods et al. | |
| 7,453,579 B2* | 11/2008 | Kothari | G09G 3/3466 356/519 |
| 7,682,311 B2* | 3/2010 | Simopoulos | G01S 15/584 600/453 |
| 7,894,126 B2* | 2/2011 | Gunter | G01N 21/3581 359/326 |
| 2004/0010196 A1* | 1/2004 | Wang | G01N 21/3581 600/476 |
| 2005/0278667 A1 | 12/2005 | Boucher et al. | |
| 2006/0103378 A1 | 5/2006 | Pakdaman et al. | |
| 2007/0046301 A1* | 3/2007 | Kasapi | G01R 31/311 324/754.22 |
| 2009/0259452 A1* | 10/2009 | Takeuchi | G06F 17/5036 703/14 |
| 2010/0306719 A1 | 12/2010 | Smayling | |
| 2011/0285577 A1* | 11/2011 | Sun | G01S 13/36 342/123 |
| 2013/0121617 A1* | 5/2013 | Serrels | G06K 9/3233 382/284 |

FOREIGN PATENT DOCUMENTS

| | | |
|---|---|---|
| JP | 2015547965 | 10/2012 |
| WO | WO-2004061725 | 7/2004 |
| WO | WO-2004061725 A1 | 7/2004 |

OTHER PUBLICATIONS

Rowlette et al., "Critical timing analysis in microprocessors using near-IR laser assisted device alteration (LADA)", Test Conference, 2003. Proceedings. ITC 2003. International, vol. 1, pp. 264-273, 2003.

Constantinescu, "Trends and challenges in VLSI circuit reliability." Micro, IEEE, vol. 23, Issue 4, pp. 14-19, 2003.

Kindereit et al. "Quantitative investigation of laser beam modulation in electrically active devices as used in laser voltage probing", Device and Materials Reliability, IEEE Transactions on, vol. 7, Issue 1, pp. 19-30, Mar. 2007.

Kindereit et al., "Investigation of laser voltage probing signals in CMOS transistors", Reliability physics symposium, 2007. proceedings. 45th annual. ieee international, pp. 526-533, Apr. 2007.

Calonder et al. "Brief: Binary robust independent elementary features", Computer Vision—ECCV 2010 Lecture Notes in Computer Science, vol. 6314, pp. 778-792, 2010.

Niu et al. "Two-photon absorption laser assisted device alteration using continuous wave 1,340 nm laser." Journal of Materials Science: Materials in Electronics, vol. 22, Issue 10, pp. 1542-1552, Oct. 2011.

Gielen et al., "Analog Circuit Reliability in Sub-32 Nanometer CMOS: Analysis and Mitigation", Design, Automation & Test in Europe Conference & Exhibition (DATE), 2011, pp. 1-6, 2011.

Stoker et al. "Pump Probe Imaging of Integrated Circuits." ISTFA 2013: Conference Proceedings from the 39th International Symposium for Testing and Failure Analysis, pp. 168-172, Nov. 1, 2013.

Matlin et al., "Non-Invasive Recognition of Poorly Resolved Integrated Circuit Elements", Information Forensics and Security, IEEE Transactions on, vol. 9, Issue 3, pp. 354-363, Mar. 2014.

PCT Search Report and Written Opinion, PCT/US2013/071231, 12 Pages, dated Aug. 19, 2014.

European Search Report for Application No. 13868949.2, dated Jul. 27, 2016, 12 pages.

* cited by examiner

METHOD AND APPARATUS FOR CONDUCTING AUTOMATED INTEGRATED CIRCUIT ANALYSIS

CROSS-REFERENCE TO RELATED APPLICATIONS

This application claims benefit of U.S. provisional patent application Ser. No. 61/772,712, filed Mar. 5, 2013 and U.S. provisional patent application Ser. No. 61/737,516 filed on Dec. 14, 2012, both of which are herein incorporated by reference.

GOVERNMENT RIGHTS IN THIS INVENTION

This invention was made with U.S. government support under contract number HR0011-11-C-0088 (DARPA). The U.S. government has rights in this invention.

BACKGROUND

Field

Embodiments of the present invention generally relate to integrated circuit analysis techniques and, more particularly, a method and apparatus for conducting automated integrated circuit analysis.

Description of the Related Art

Modern integrated circuits are very complex. When an integrated circuit fails, or if it does not function as expected, isolating the reason for failure of the integrated circuit is very challenging. Often, large amounts of design information are used to trace the origin of a failure to physical device characteristics that lead to the failure. Once that is accomplished, local analysis of the devices may be possible to perform using standard probing tools. One of these tools often uses laser probing techniques with laser scanning microscopes. When using laser probes, it is necessary to navigate to a specific region of an integrated circuit with the help of the design information (usually in the form of a netlist or layout schematic) to noninvasively measure electronic waveforms (either the RMS power or the actual time-dependent waveform), and determine if that waveform is anomalous or not. These tools are often used by highly trained technicians who manually navigate around the device and collect waveforms. The technicians then compare the waveforms to simulations to determine if there was an error. Such manual analysis is time consuming and costly. Moreover, these methods are restricted to devices where a significant amount of design knowledge is available to the technicians. In cases where the design is not known, it is necessary to destructively reverse engineer the device to determine the design prior to performing analysis of the functionality. Destructive reverse engineering processes are undesirable, because they leave the device in a non-functioning state. In some instances, it is possible to combine the destructive reverse engineering step with standard laser probing to identify the design of the IC, however successful alignment of data from electron microscopes and laser probing microscopes requires manual user input.

There is a highly varying degree of device geometry visibility between idealized layout files, electron microscope images, and optical images. In particular, integrated circuits that are manufactured by third parties may contain features that are smaller than the diffraction limited spot size of the imaging system. In those cases, little design information is known and standard recognition methods are not effective because the unaided imaging system cannot resolve sufficiently detailed images to accurately recognize logic elements in the integrated circuit. Moreover, geometry alone is an insufficient parameter for device analysis. Standard destructive methods that focus only on geometric details are unable to efficiently detect process-related deficiencies that are intermittent or caused by device stress due to heat, age or other physical causes Therefore, there is a need in the art to develop generalized device analysis methods that can automatically identify and isolate faults, even when full device design information is unavailable.

SUMMARY OF THE INVENTION

Embodiments of the present invention generally comprise an apparatus and/or method for conducting non-invasive automated integrated circuit analysis, substantially as shown in the and/or described in connection with at least one of the figures, as set forth more completely in the claims.

The various advantages of the non-destructive analysis approach, aspects and novel features of the present disclosure, as well as details of an illustrated embodiment thereof, will be more fully understood from the following description and drawings.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

DETAILED DESCRIPTION

Embodiments of the present invention comprise a method and simultaneously scannable dual laser confocal microscope apparatus for conducting automated integrated circuit analysis. The apparatus employs a plurality of methods in order to create a plurality of images of an integrated circuit collected under varied operational conditions, which are then combined and stored in a database as a hyper-dimensional representation (also referred to as hyper-dimensional imagery) of the integrated circuit under test. A recognition algorithm processes the hyper-dimensional imagery stored in the database structure to extract the presence and identity of logic cell elements of the integrated circuit under test. To expedite the analysis, the recognition algorithm operates a control loop that sequentially detects the location of device activity within a logic cell followed by detection of electronic waveforms at those locations that exhibit sufficient activity above a threshold. From the analysis of the combined logic cells and waveforms, a netlist is generated representing the integrated circuit under test. In some embodiments, the netlist is formatted in SPICE, Verilog format, or any format known to those of ordinary skill in the art. Moreover, additional capabilities to probe electrical connections, enhance particular features of interest, or improve the overall fidelity of the netlist are enabled by the apparatus, upon which all of the above methods operate.

Figure 1:
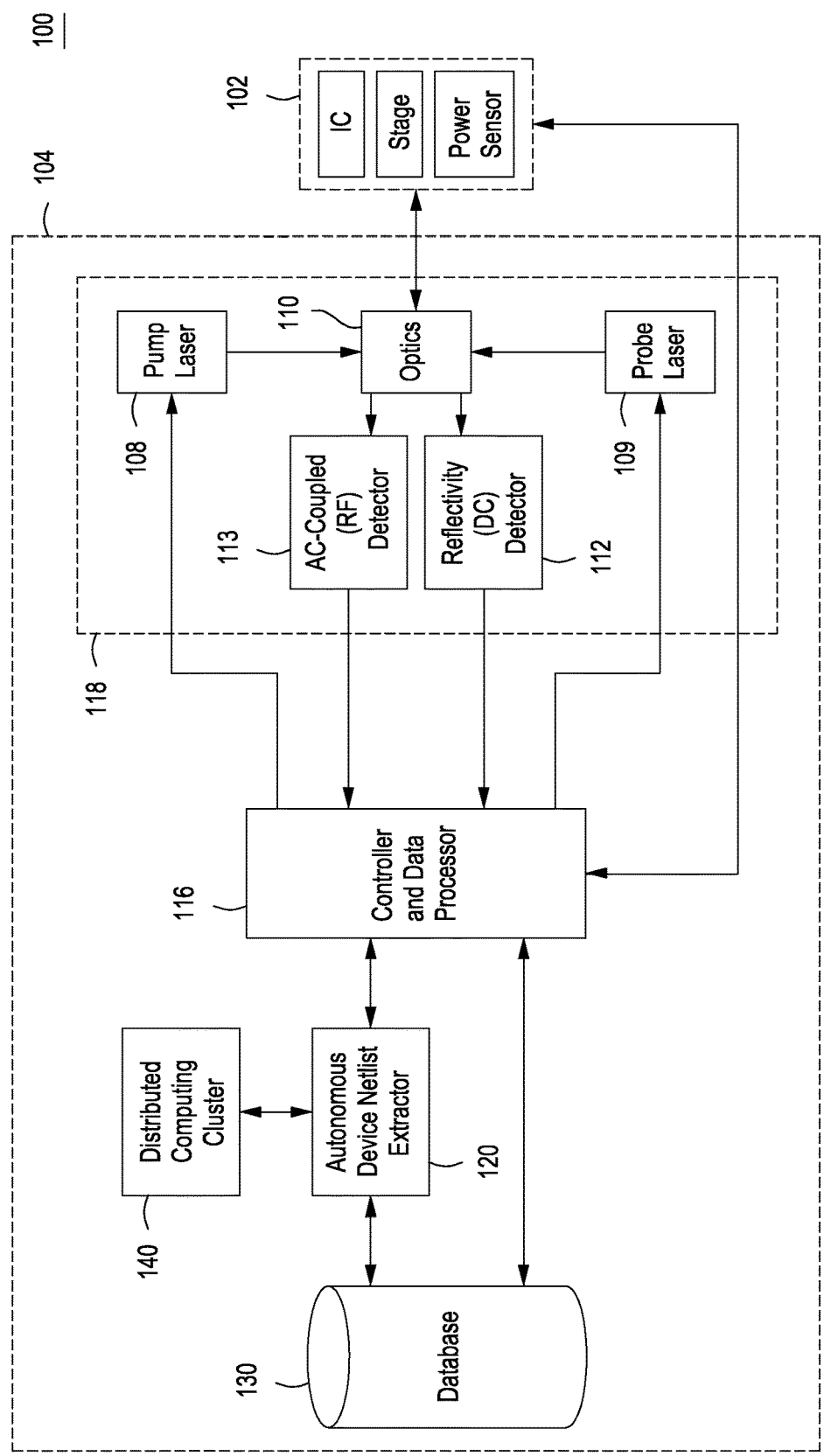
FIG. 1 depicts a block diagram of an system for conducting automated integrated circuit analysis in accordance with at least one embodiment of the invention.

FIG. 1 depicts a block diagram of a system 100 for conducting automated integrated circuit analysis in accordance with at least one embodiment of the invention. The system 100 comprises an analyzer apparatus 104 and an integrated circuit (IC) assembly under test 102. The IC assembly under test 102 comprises a functional integrated circuit mounted to a 6-axis (x, y, z, angle1, angle2, angle3) positioning stage. The analyzer apparatus 104 comprises a pump/probe assembly 118, a controller and data processor 116, autonomous device netlist extractor 120, distributed computing cluster 140, and database 130. The pump/probe assembly contains pump laser 108, probe laser 109, optics 110 for simultaneously scanning and coupling the pump and probe beams, DC reflectivity emission detector 112 and AC-coupled RF emission detectors 113. As is described in detail below, the analyzer apparatus 104 is capable of performing several types of laser scanning of the IC under test 102, whereby the pump laser is able to locally change the way the device functions, by altering the timing or logic state of the device 102, while simultaneously measuring the effect of the change elsewhere on the device 102 using the probe laser. The pump/probe assembly 118 generates a plurality of images of the IC under test. The pump/probe images and waveform data are then stored and combined with standard DC reflectivity images and electronic waveform data by the autonomous device netlist extractor (ADNE) 120 to create a netlist of the integrated circuit under test. According to exemplary embodiments, the controller and data processor 116 processes the measured RF power from the AC-coupled RF emission detectors 113 (which measure RF in selected frequency ranges) to produce a spatio-temporal evolution of the voltage on the integrated circuit under test as an activity map. The ADNE 120 may use the activity map to determine interconnections between elements of the integrated circuit under test.

The pump/probe assembly 118 forms a laser-scanning microscope that scans a focused probe laser 109 over the integrated circuit (IC) under test 102 while simultaneously altering the functionality of the IC 102 using the pump laser 108. The simultaneous scanning and altering of functionality adds additional dimensions to the hyper-dimensional imagery of the IC under test 102, resulting in increased accuracy of logic cell detections. According to some embodiments, there may be a plurality of scanning laser microscopes, each configured to scan the same field of view of a device. Hyper-dimensional imagery can be either collected passively, whereby while the IC 102 is not powered, or actively, whereby the IC 102 is powered and operated with the controller and data processor 116. The pump/probe assembly 118 uses the pump laser (a first laser) to pump a selected region of the integrated circuit under test with photocarriers and uses the probe laser (a second laser) to monitor the effect the pumping has on the integrated circuit under test. According to some embodiments, the laser used to generate the plurality of images is at least one of continuous wave, modulated, or a pulsed laser.

Scanning is performed from the backside of the integrated circuit in order to directly observe the distribution of the logic cells. Some device preparation for backside scanning is typically necessary and described below. As the focused pump laser beam from pump laser 108 passes over the integrated circuit under test in 102, the laser beam causes changes in the integrated circuit electrical characteristics generating photo-carriers or heat within the integrated circuit electronics. These changes are monitored by a second laser and laser detector. Using various scanning techniques, the pump/probe assembly 118 produces optical and waveform information (hyper-dimensional imagery) that can be used to identify integrated circuit elements and their interconnections. Each component of the analyzer apparatus 104 is described with respect FIGS. 2-6 below and operation of the analyzer apparatus 114 is described with respect to FIGS. 7-11 below.

Figure 2:
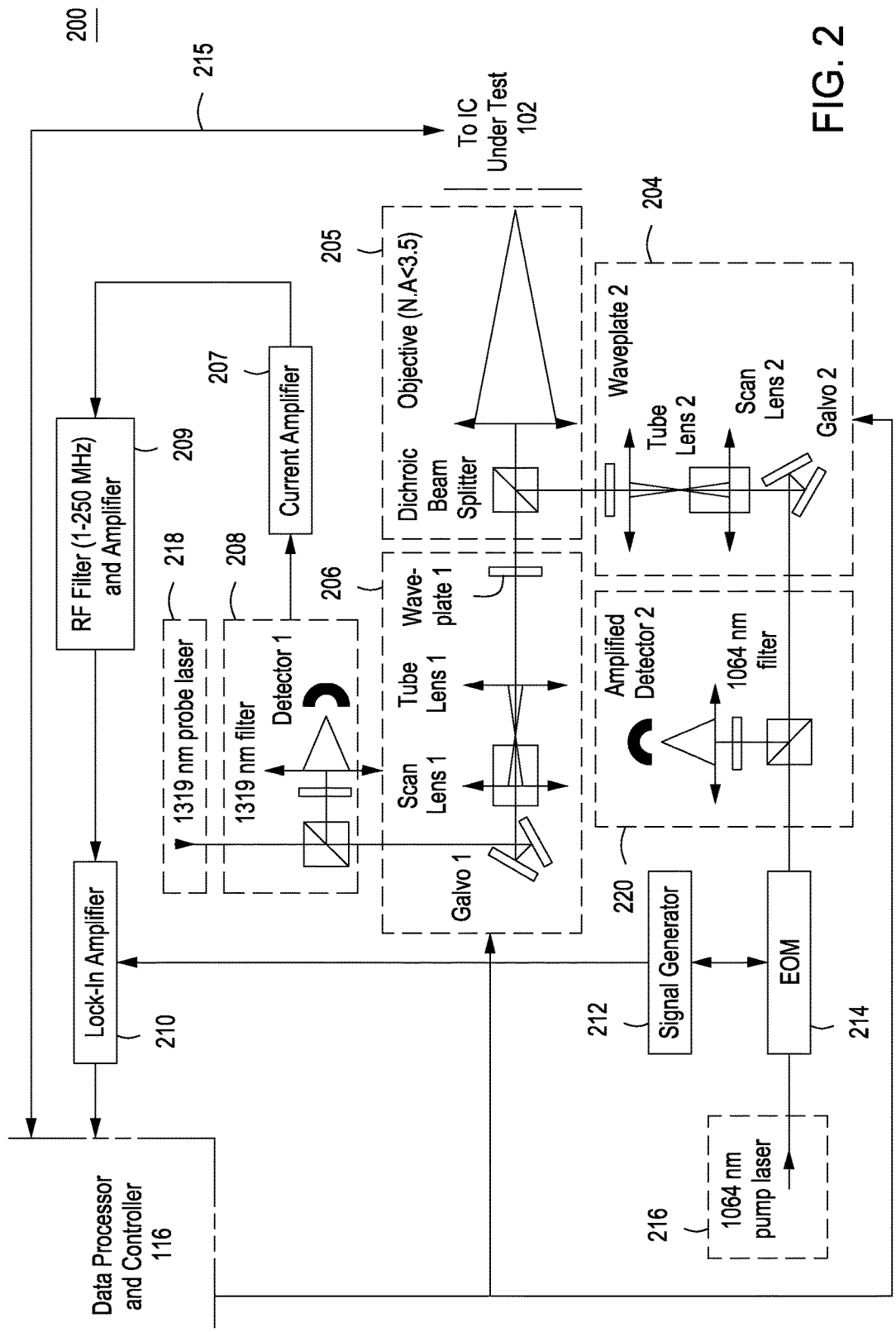
FIG. 2 depicts a block diagram of the pump probe assembly of FIG. 1 in accordance with at least one embodiment of the invention.

FIG. 2 depicts a block diagram of the pump/probe assembly 118 of FIG. 1 in accordance with at least one embodiment of the invention. In one embodiment, the pump/probe assembly 118 comprises a lock-in amplifier 210, RF filter and amplifier 209, current amplifier 207, probe laser 218, probe detection optics 208, probe scan optics 206, coupling optics 205, pump scan optics 204, pump detection optics 220, pump modulator 214, pump laser source 216, and signal generator 212.

The pump/probe assembly 118 utilizes various wavelengths of laser light, various scanning patterns, and various laser modulations to produce a plurality of images of the integrated circuit under test 102. This hyper-dimensional imagery facilitates performance of a multimodal image analysis resulting in a detailed representation of the integrated circuit which can be used to distinguish circuit features with greater fidelity than any single image. In one embodiment, the first and second lasers 216 and 218 have two different wavelengths, for example, 1064 and 1319 nm. Those of ordinary skill in the art will recognize that these frequencies are merely exemplary and are not limiting. Depending on design choice, neither, both or one of the lasers 216 and 218 may be amplitude, frequency or phase modulated. According to other embodiments, the lasers 216 and 218 may be mode-locked ultrafast lasers with pulse lengths ranging from 100 fs (femtoseconds) to 100 ps (picoseconds).

In the embodiment depicted in FIG. 2, the probe laser 218 has a wavelength of approximately 1319 nm and is not modulated, while the second pump laser 216 has a wavelength of 1064 nm and is amplitude modulated (e.g., pulsed) using modulator 214 and signal generator 212. The laser beams respectively pass through microscope optics 204 and 206 and transmit through common optics 205 including a dichroic beamsplitter and high variable numerical aperture air gap or solid immersion lens objective and focus on one or more of the active device layers within the IC 102, e.g., the layer containing the poly gates. Reflected laser light travels back through the microscope optics 204 and 206 which separate the pump and probe return signals to be refocused onto emission detectors using optics in probe laser detectors 208 and 220. The structure of the components used to receive the lasers may vary within scanning type and other factors. In one embodiment, the output of the probe laser detector 208 is coupled to a current amplifier 207 and passed to a lock-in amplifier 210 that is synchronized to the signal generator 212, whose output is directed to an ND converter 200, which shares a readable memory with the controller and data processor 116. Similarly the pump laser detector signal is amplified and also directed to detection electronics in the controller and data processor 116. According to one embodiment, the device may be operated using digital input/output lines 215 during scanning. Similarly, galvanometer 1 and galvanometer 2 used to scan the lasers 216 and 218 are operated from the controller and data processor 116. In this fashion, the very small response of the circuit to the pump laser is sensed and amplified and corresponding data is communicated to the database 130 through the ADNE 120.

Charge flow imaging is realized by locking the probe laser to the pump repetition frequency. Charge flow imaging is a method used to enhance different features within the IC 102 in order to improve logic cell detection by imaging the feature's response to injected charge carriers. Charges are injected locally by the pump laser at a fixed frequency (typically 1-500 MHz), and the probe laser is tuned to that same frequency. Small signals generated by the pump laser are sensed when the lock-in amplifier 210 is tuned to the same pump frequency. Images of the device produced at the pump laser frequency then reveal the charge flow throughout the IC which can be used to resolve additional features in an IC such as the polysilicon gates.

The phase imaging method is a further refinement of the charge flow method which further highlights the contrast between different components within the IC 102. Phase imaging is achieved by uniquely color-coding the phase of the lock-in signal and plotting the detected color-coded phase as a function of probe laser coordinate.

Figure 3:
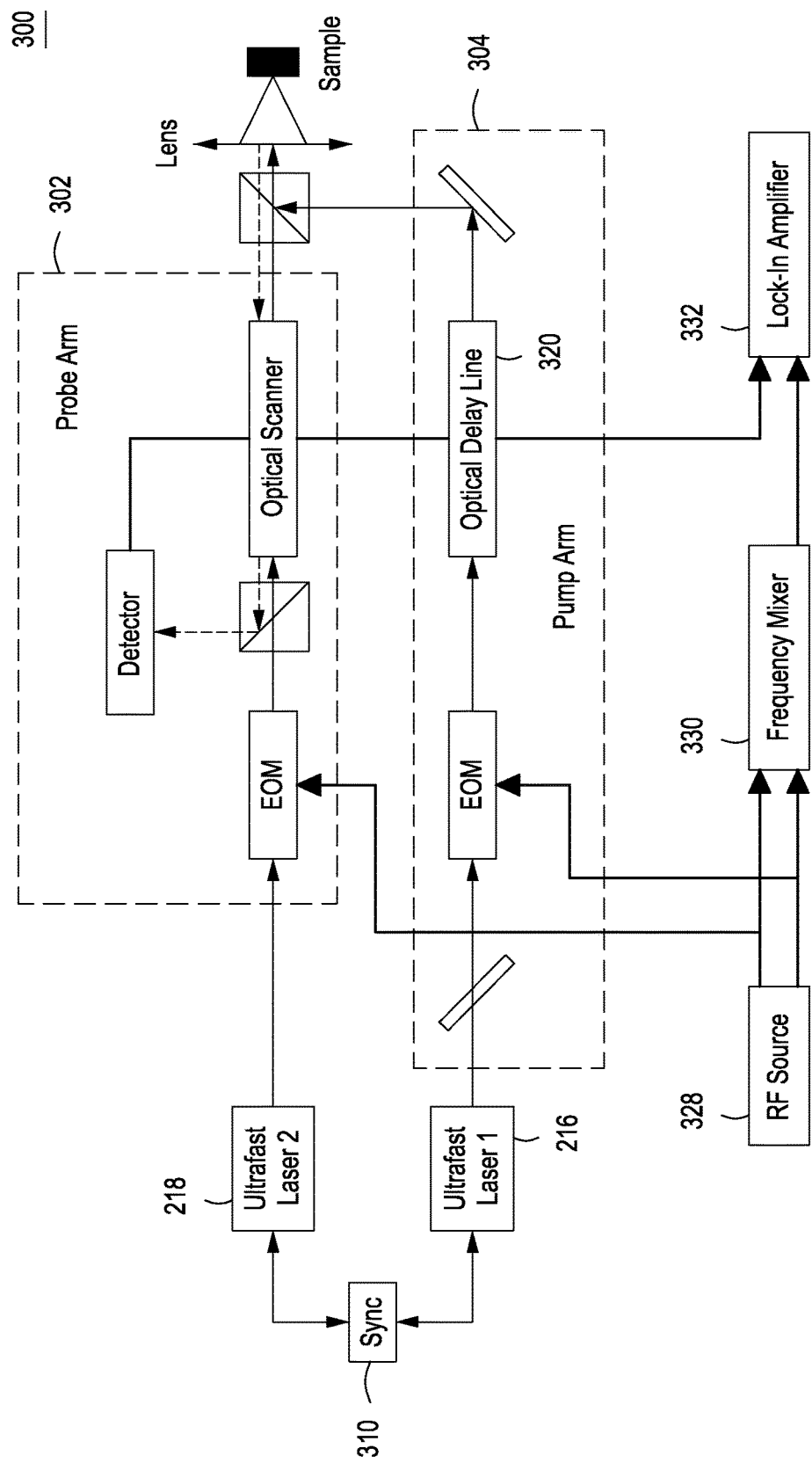
FIG. 3 depicts a block diagram of one ultrafast laser pump/probe detector assembly of FIG. 1 in accordance with at least one embodiment of the invention.

In a second embodiment shown in FIG. 3, charge flow imaging is achieved on picosecond time-scales to allow glimpsing the position of the charge carriers as they move away from the injection point created by the pump laser (e.g., pump laser 216 shown in FIG. 2). In the depicted embodiment, the pump laser 218 and the probe laser 218 are mode locked and synchronized. In the depicted embodiment, the pump laser 216 and the probe lasers 218 are optionally derived from the same source laser. The ultrafast laser is split into a pump arm 302 and a probe arm 304, and the pump arm 302 and the probe arm 304 are independently modulated. The resulting pump/probe signal is measured again at a lock-in frequency that is given by the sum or difference of the two modulation frequencies, or one of its harmonics.

The arrival of the optical signals on the pump and probe arms can be adjusted in order to observe the charge location in the device containing the IC 102 at various fixed points in time following the arrival of the pump. The unique material-specific temporal response to injected free carriers enhances material contrast within the IC by adjusting the relative delay between the pump arm 302 and the probe arm 304. In this way, the dynamic nature of charge flow through the device, as well as corresponding thermal transport on sub pico-second times scales can be observed. The enhanced material contrast directly improves the performance of registration and object recognition algorithms. During testing, the laser beams are scanned in accordance with a specific pattern across the surface of the integrated circuit under test 102. In one embodiment, the scanning is performed by the microscope optics 204 and 206 using two, independently adjustable mirror pairs (galvanometers). While scanning is occurring, the integrated circuit under test may be powered and also have test signals generated from within the data processor and controller 116 and supplied by digital input/output lines 215 (known as test vectors) applied to the integrated circuit input ports. As such, additional information may be gathered based upon whether or not the integrated circuit is powered during a laser scan, or has specific sets of test vectors being applied during laser scanning. Each state of the integrated circuit while being scanned may result in a separate image to be used in the multimodal analysis. Details of the operation of the pump/probe assembly 118 during scanning of the integrated circuit under test 102 are described with reference to the figures below.

A second method enabled by the embodiment in FIG. 2 is referred to as "waveform suppression". In this embodiment, the lock-in detector is bypassed and the amplified and filtered RF signals from the amplifier 209 are measured directly by electronics in the Data Processor and Controller 116. In waveform suppression, an active device 102 is stimulated by test vectors generated by the data processor and controller 116. Connections between logic cells are directly observed by selectively de-activating logic cells by fixing the focus of the pump laser 216 at the output of the logic cell. While holding the pump laser fixed at the logic cell output, the probe laser can identify those logic cells that are connected to the de-activated logic cells by measuring changes in the waveform. By iteratively pumping the output of all those previously suppressed (as detected by the probe laser) logic cells, one can determine the unique network of connections between active logic cell elements.

FIG. 3 is a block diagram of an ultrafast laser embodiment of the pump/probe assembly 118 of FIG. 1, in accordance with exemplary embodiments of the present invention. Waveform suppression can be applied using the pulsed laser system 300. One form of waveform suppression is referred to as "waveform modulation". In "waveform modulation", first, the pulse repetition of two ultrafast lasers is synchronized with a synchronization unit 310. Alternatively, one may separate a portion of a single laser source to be used as the probe. In this embodiment, both the pump and probe laser pulse trains are amplitude modulated by an RF source 328 at different frequencies. The relative arrival time of the two pulses is controlled using an optical delay line 320. Finally the signal is measured using a frequency mixer 330 and lock-in amplifier 332 before the signal is sent to the data processor 116. The early arrival of one pulse is then used to affect the output of one logic cell of interest, and the temporal response can be measured elsewhere in the IC with the probe at a later time determined by the optical delay line 320. Subsequently, important parameters of the device are extracted such as the local time delays between two logic cells and local electrical impedance, which are in turn used to isolate timing errors or characterize how local variations in the manufacturing process affects device performance.

Figure 4:
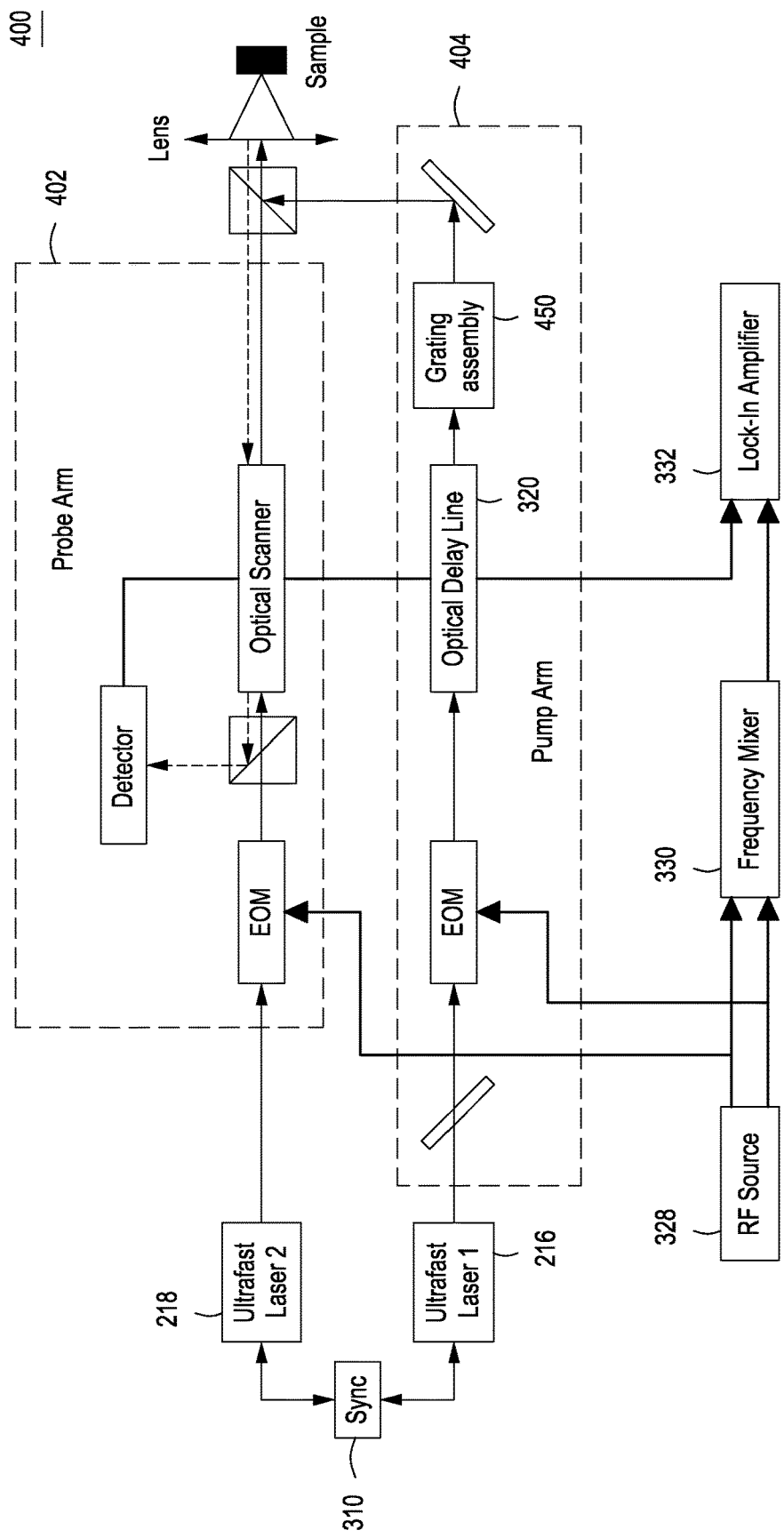
FIG. 4 depicts a block diagram of the system and apparatus for performing super-resolved imaging in accordance with at least one embodiment of the invention.

FIG. 4 depicts a block diagram of the system 400 for performing super-resolved imaging in accordance with at least one embodiment of the invention. The system 400 comprises a probe arm 402 and a pump arm 404, where the structured probe arm laser is laser 218, an ultrafast laser and the structured pump arm laser is laser 216. Lasers 216 and 218 are synchronized via synchronization unit 310. A grating assembly 450 or similar wavefront distortion device (e.g. holographic plate, wavefront distortion device, or phase plate) is optionally inserted in the pump arm 404 of the ultrafast pump-probe imaging system 400, in addition to the components shown in FIG. 3. In this way, the pump arm 404 is able to project a pattern of carriers onto the integrated circuit which can then be observed by the probe arm 402 of the microscope. This particular embodiment in FIG. 4 enables a type of super-resolved imaging method (to be described below) whereby the several images created by varying patterns of injected charge carriers in the integrated circuit are used together to develop an image of the IC under test that has an improved resolution compared to any single image of the device.

Figure 5:
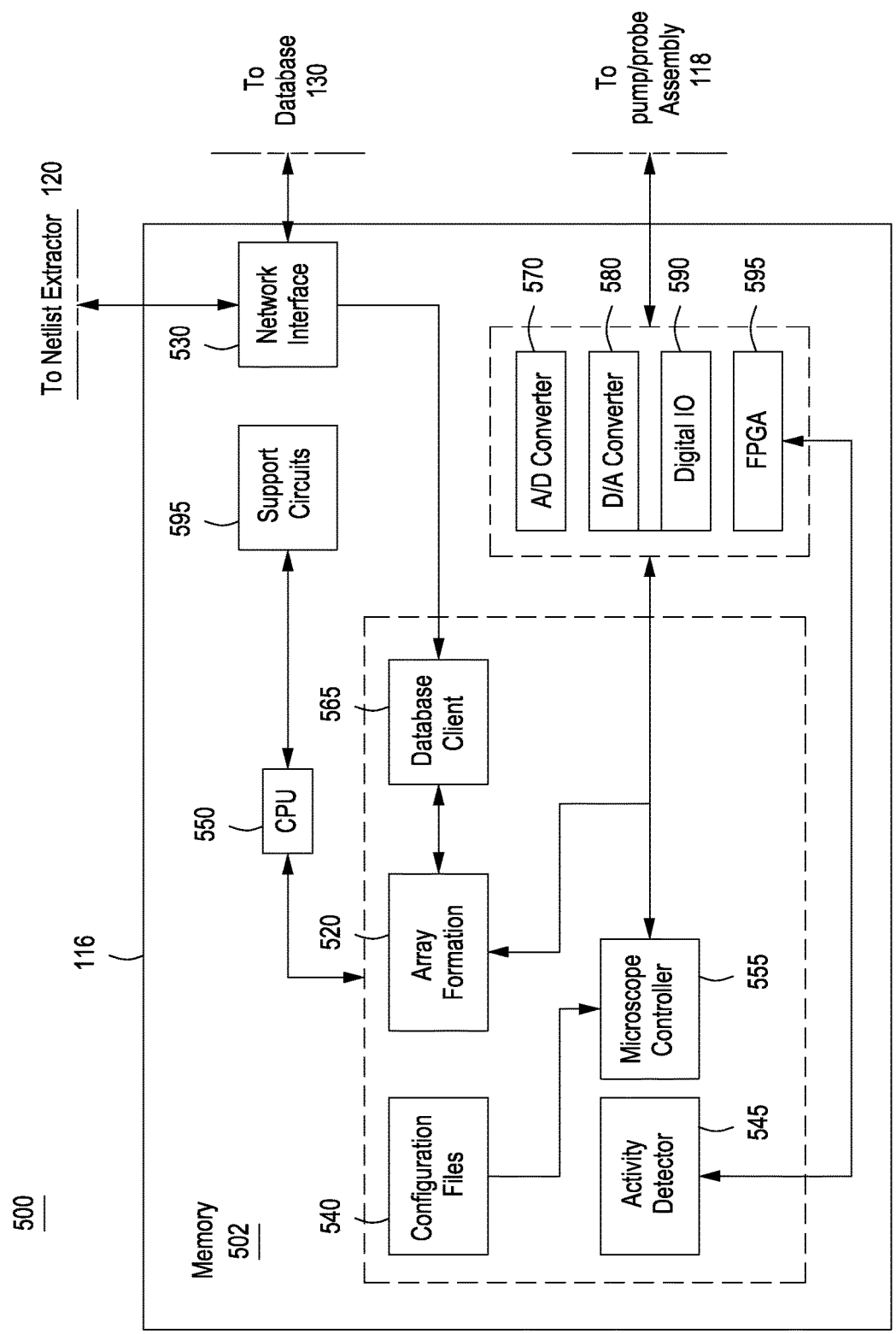
FIG. 5 depicts a block diagram of the data processor subsystem in accordance with at least one embodiment of the invention.

FIG. 5 depicts a block diagram of the controller and data processor 116 of FIG. 1 in accordance with at least one embodiment of the invention. The controller and data processor 116 may be a general-purpose computer with memory 502 containing stored data and executable code that perform several functions comprising sensing and sending data to the pump/probe assembly 118, communication with the autonomous device netlist extractor 120 or the database 130 over a network connection 530. The controller and data processor 116 comprises a central processing unit (CPU) 550, a memory 502 and support circuits 595. The memory 502 stores array formation 520, configuration files 540, activity detector 545, microscope controller 555 and a database client 565. The processor 116 further comprises devices 560. The devices 560 comprise an ND converter 570, a D/A converter 580, a digital IO 590 and an FPGA 596. The database client 565 communicates with the database 130 via the support circuits 595 and the network interface 530. Signals are sent back and forth to the pump/probe apparatus over the devices 560. Galvanometer controls and laser scanning signals are handled by analog to digital (ND) converter 570 and digital to analog (D/A) converter 580. Digital signals used to operate the IC under test 102 are handled by a digital I/O device 590. The microscope controller 555 coordinates and executes all experiments with the pump/probe apparatus by reading arrays from one or more configuration files 540 that are used to set the microscope stage coordinates (region of the IC to examine), galvanometer coordinates (scan field of view), desired microscope objective, test vector set, or other equipment settings such as the power supplied to the circuit or drawn by the circuit. Commands are facilitated through the use of one or more CPUs (central processing units) 555 and support circuits 595. RF signals may be digitized and transferred to the FPGA to carry out rapid signal analysis. For example, the FPGA may be used to trigger the pump/probe assembly to acquire a signal when an RF signal of a certain characteristic is sensed by the signal-based triggering may be used by the FPGA to acquire The components of the control system and data processor 500 work together to form data arrays 520 consisting of tuples of configuration parameters and measurements. Generally speaking, data arrays (tuples) are passed to the database 130 from the database client 565 over a network via the network interface 530, but to expedite data acquisition it is critical to acquire and transmit only critical data to the database. Such a case may occur for those data sources present only in a subset of the device 102. One example of that type of data source is the electronic waveform measured from the probe detector arm, wherein acquisition may require averaging of many hundreds or thousands of waveforms. In that case, significant time can be saved by acquiring if certain types of signals only if there is an indication of the presence of the signal and only in regions of the IC under test where those signals can be generated. To achieve this goal, the control system and data processor 500 also contains an Activity Detection algorithm 545, present either in memory 502 or programmed onto an FPGA 596, which is able to both determine with fewer samples than a waveform whether there exists a waveform at all and where the optimal location to acquire waveforms is within the particular field of view. Further improvements to the waveform acquisition rate are enabled by communication using a Database Client 565 with the Auto-DNE subsystem 120, which is able to populate the configuration files 540 with candidate locations for acquiring waveforms based on the presence of detected components in the field of view, i.e. logic cells. The database 130 contains metadata for the various detected logic cells, including precise locations where waveforms will be present. The back and forth transfer of information between the Auto-DNE 120 and the controller and data processor 116 (embodied as system 500), including intermediate analysis by the Activity Detector 545, enables system 500 to perform autonomous operation of the IC analysis through methods that will be outlined below.

The support circuits 595 may comprise one or more well-known circuits that facilitate and support the functionality of the CPU 550. Such circuits include, but are not limited to, clock circuits, input/output circuits, cache, buses, communications circuits, peripheral drivers and the like.

Figure 6:
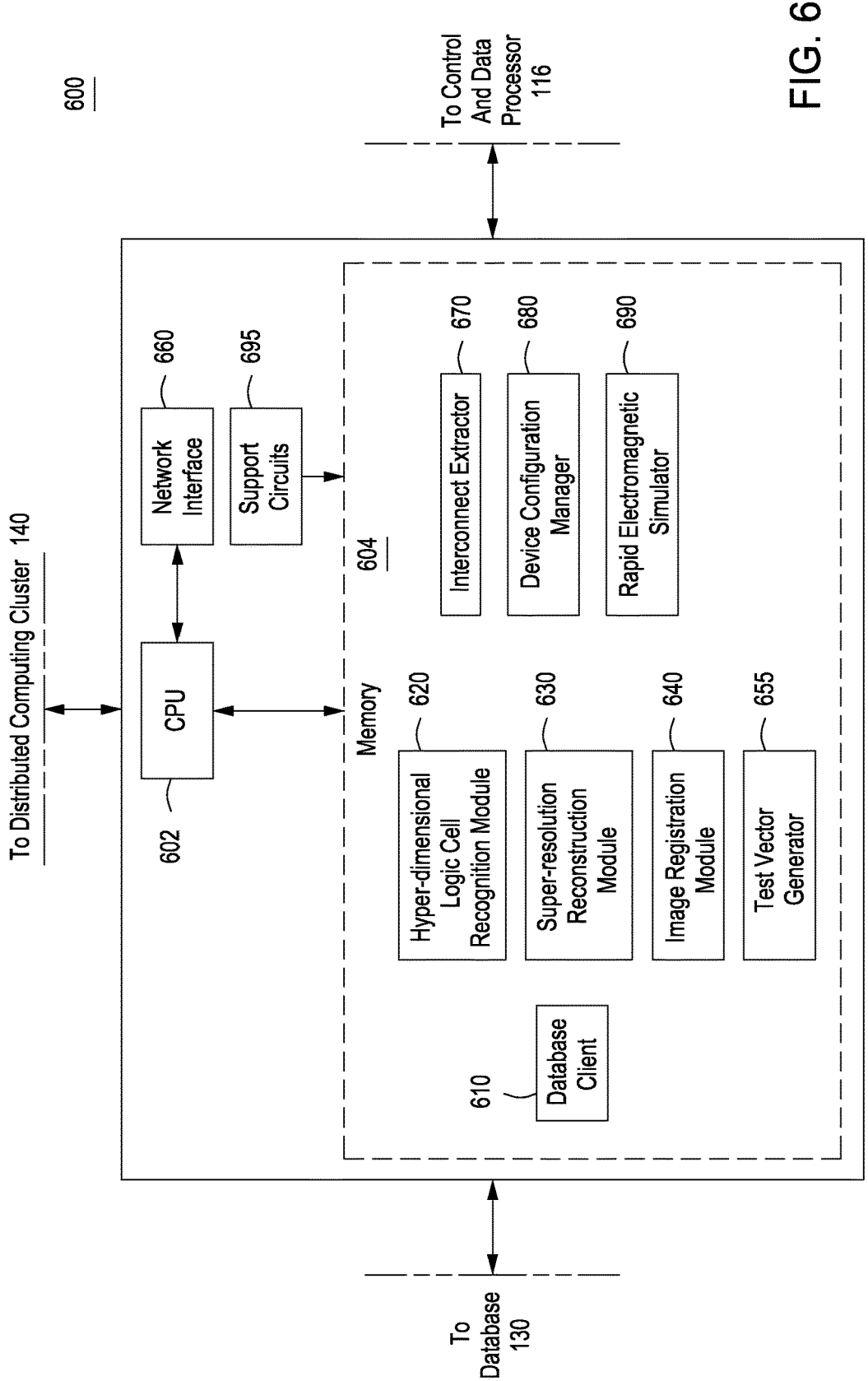
FIG. 6 depicts the autonomous device netlist extractor subsystem in accordance with at least one embodiment of the invention.

FIG. 6 depicts the autonomous device netlist extractor subsystem in accordance with at least one embodiment of the invention. The Autonomous Device Netlist Extractor 600 comprises a CPU 602, memory 604, support circuits 695 and a network interface 660. Memory 604 may comprise well-known memory devices including random-access memory and read-only memory. The memory 604 stores executable code and data to enable the CPU 602 to produce a netlist for the IC under test 102 using the analyzer apparatus 104. The memory 604 comprises a Database Client 610, a hyper-dimensional logic cell recognition module 620, super-resolution reconstruction module 620, an image registration module 640, a test vector generator 655, an interconnect extractor 670, a device configuration manager 680, and a rapid electromagnetic simulator 690. Each of these controllers, analyzers, imagers, and generators may be implemented as individual software modules or may be a portion of a larger singular software module. In either instance, these modules or portions thereof are executed by the CPU 602, with the assistance of support circuits 695, to cause the Autonomous Device Extraction Unit 600 to perform various methods in accordance with various embodiments of the invention.

The distributed computing cluster 140 is any well-known network of computing elements, each containing memory and any number of CPUs, GPUs, FPGAs, ASICs, or similar. They are programmed to work together to analyze larger volumes of data than can be stored on any computer. It is used for two of the main methods of this invention. First, the distributed computing cluster is used to correlate RF waveform signals collected at various locations in the IC. Correlations are then returned to the auto-DNE and used to identify connected logic cells and construct the device netlist. Secondly, the distributed computing cluster is used, in a novel method, to execute electromagnetic field simulation code that is used to predict how the logic cells will appear when acquired by the pump-probe assembly.

The database 130 is any relational database that contains both logic cell libraries (including functional Verilog, 2D layer geometry, and process parameters) and data acquired by the pump-probe assembly 118 and processed by the controller 116, which are then used at a later time by the auto-DNE 120 to carry out any number of the main methods described herein and construct a netlist.

Figure 7:
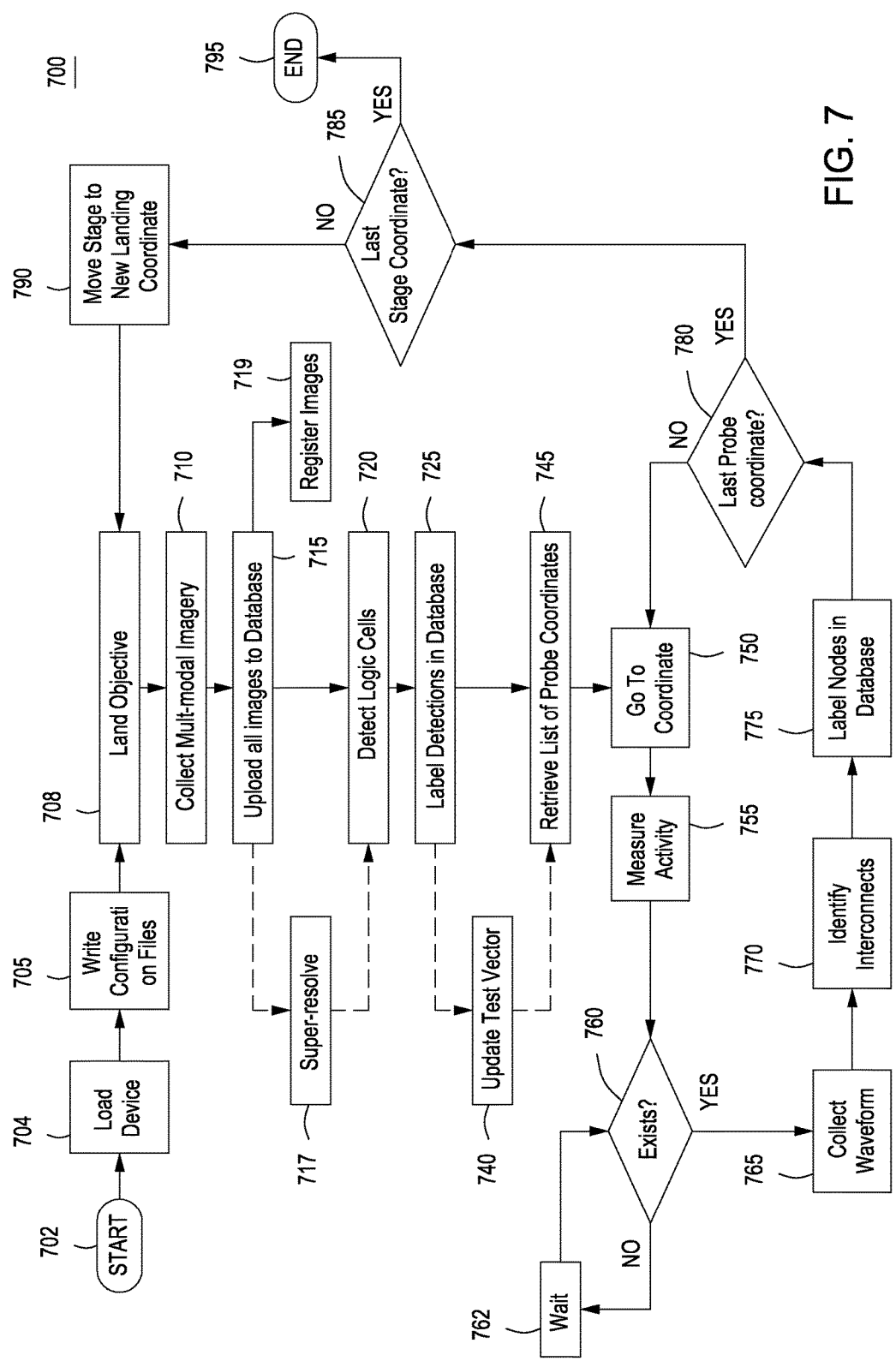
FIG. 7 depicts a flow diagram of a method for automatically and non-invasively extracting a device netlist in accordance with at least one embodiment of the invention.

FIG. 7 depicts a flow diagram of a method 700 of performing automated integrated circuit analysis in accordance with at least one embodiment of the invention. The method 700 (representing one embodiment of the function of hyper-dimensional logic cell recognition module 620) begins at step 702 and proceeds to step 704 wherein the integrated circuit under test is prepared for analysis. Step 704 includes packaging the chip so that the back surface of the chip (the substrate) faces upwards, followed by polishing the exposed back surface of the silicon substrate to an optical quality finish.

Once the integrated circuit under test is prepared and coupled to the system 100, method 700 proceeds to step 705 wherein the ADNE algorithm writes configuration files to the probe assembly computer. These configuration files include a list of landing locations and experimental parameters such as microscope objective, laser source, measurement type and the like, which allow the pump/probe assembly to begin collecting data.

The pump probe assembly 118 then positions the sample under the appropriate microscope objective in step 708 and then proceeds to collect several different images of the device including both pump/probe images (e.g. charge flow images, time-resolved charge flow, etc) lands an objective on a location of interest. The method 700 then proceeds to step 710, wherein the system 100 collects several multimodal images of the same region of the device using either one or both of the pump-probe lasers. Multi-modal images are collected according to standard imaging methods used in failure analysis (FA) such as 1064 nm and 1319 nm reflectivity, laser-induced voltage alteration (LIVA), optical beam induced current (OBIC), thermally induced voltage alteration (TIVA), pump-probe images such as charge flow, time resolved charge flow, AC or DC reflectivity scans, AC or DC absorption scans, single point scans while varying test vectors, scans at a plurality of laser wavelengths, stress mapping, or the like. At step 715 the images are uploaded to the database 130, where they are registered or super-resolved in step 717. Logic cells are detected in step 720 from one or more of the images collected at the landing site (using a third novel hyper-dimensional recognition approach). In step 725, labels for each detected logic cell are entered into the database 130. After detections have been carried out, a list of probe locations is written into the pump probe assembly configuration files before the microscope moves to the next landing using the known input and output node locations in the logic cells.

For each probe coordinate, a test vector set is provided to the IC, which initially is a repeating random set of test vectors produced at the input pins of the chip. First, activity is measured in step 755 using an activity measurement method to be described below. If activity is detected to exist at step 760, we integrate longer and collect a waveform at step 765. If activity is not detected, the method 700 proceeds to step 762, where the method 700 waits for activity. The correlation between the immediately measured waveform is used by the interconnect extractor 670 shown in FIG. 6 in step 770 to identify connected nodes via correlation with other waveforms in the device. Any discovered connection is then uploaded to the database 130 to indicate, for the detected logic cell in question, what node is connected to a given input and output port on every active logic cell. This procedure repeats until all entries in the configuration files corresponding to probe and stage coordinates have completed, as determined by step 785. If additional landing locations are in the queue then the objective is relocated at the coordinate. At that point, the method 700 repeats using a new set of test vectors that are generated from the netlist information generated by the initial approximation of the netlist. When all the ports on active logic cells have been assigned to a netlist node, the process terminates at step 795.

The super-resolution reconstruction module 630 may be used in the method 700, the automated netlist extraction algorithm. The method utilizes the ultrafast embodiment of the pump/probe assembly 118 where the pump laser is a near infrared laser of wavelength ranging from 1.0-1.1 microns. The pump probe apparatus is configured to create several well-defined sinusoidal patterns of injected charge carriers which are imaged less than 1 pico-second later by the arrival of a probe pulse. The charge flow patterns are created by locking to the sum or difference frequency of the pump and probe modulation frequencies. Several images are created by rotation and changing the phase of the pump laser. The pattern of charge carriers creates an illumination grating, which down-shifts high spatial frequencies into the optical acceptance bandwidth of the system. The algorithm then un-shifts each image using an estimate of the superimposed charge carrier pattern. A large bandwidth frequency domain representation of the scene is constructed through an estimation of the overlap. Finally, a higher resolution images is created by Fourier transforming the large bandwidth frequency domain image into the spatial domain. The aforementioned method is similar to structured illumination microscopy, although the apparatus and physical process used to create the structured pattern is unlike the previous setups which use laser excited fluorescence to generate a signal. Moreover, structured illumination has previously been limited to biological applications. Here the pump-probe apparatus allows for a new application of a similar algorithm to be applied to charge-flow imaging.

Figure 8:
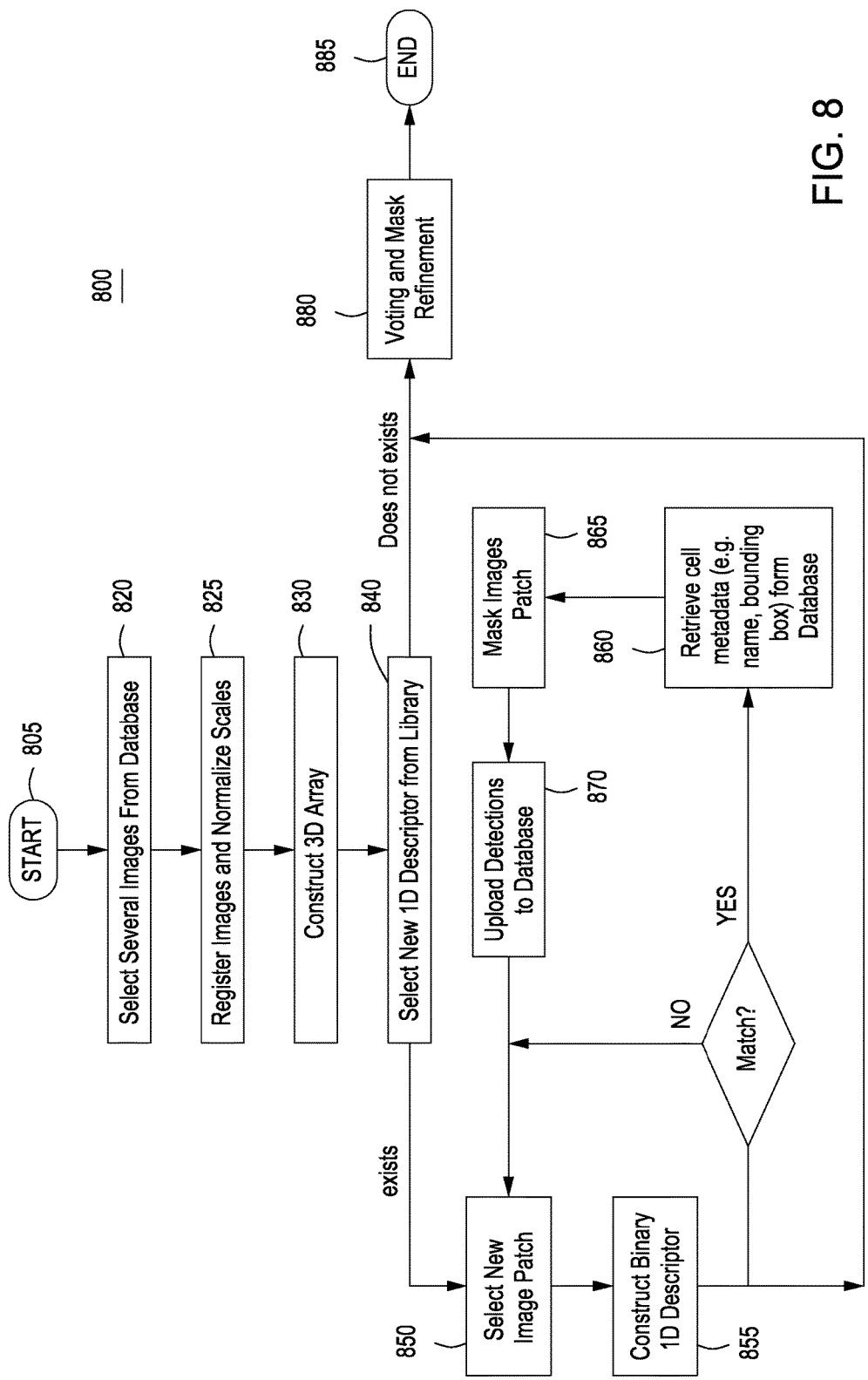
FIG. 8 depicts a flow diagram of a method for detecting logic cells using a recognition algorithm in accordance with at least one embodiment of the invention.

FIG. 8 depicts a flow diagram for a method 800 for detecting logic cells in accordance with exemplary embodiments of the present invention. The method 800 is an implementation of the method step 720 from method 700 shown in FIG. 7. The method 800 begins at step 805 and then proceeds to step 820, where several raw images are selected of the same region of the device 102 acquired with the various sensors in the system 100 shown in FIG. 1. In step 825 the multiple images are aligned and rescaled so that each array coordinate in each image corresponds to the same location on the actual device. Once properly aligned, a 3D array is constructed in step 830, in which two of the three coordinates correspond to the x and y coordinates of the plan view of the chip on device 102 and the third is an index corresponding to each of the raw images in the database 130. For each object in the database 130, 1D descriptors (see, for example, BRIEF, SWIFT, HOG) exist for each imaging modality. In step 840, the 1D descriptors are selected from the query object, which correspond to the imaging modalities selected from the raw images of the landing location stored in the database 130. If the descriptor exists, at step 850, the 3D array is iteratively scanned corresponding to the landing location imagery by selecting a sequence of regions of interest of the landing location with the same size as the query object, including all vertical and horizontal reflections of the query object. The method then proceeds to step 855, where a descriptor is constructed for each region of interest and image modality and compared to the query descriptor for each corresponding modality using any variety of methods, e.g. summing the NOR value for each bit. If the 1D descriptor and the selected descriptor do not match at step 857, then the method proceeds to step 850. If the descriptors match at step 857, the method proceeds to step 860. Those of ordinary skill would recognize that matching descriptors indicate that similarity above a threshold value is observed between the two descriptors. At step 860, logic cell metadata, for example, name, bounding box, or the like, is retrieved from database 130. At step 865, the image patches are masked and the detections are uploaded to the database at step 870. Subsequently, one of the tables (e.g. the detections table) in a suitable relational schema, are given a detection ID and a library ID entry which uniquely relates a library element to a set of pixels in each raw data image. This process repeats for all desired query objects until a set of masks for the landing region is created. Finally, overlapping masks are eliminated using a voting scheme in step 880. The process ends at step 885 after all library objects have been identified in the landing location, and for every (x, y) coordinate where a library object has been identified, there exists an entry into a relational schema that can be queried to determine what object exists within that raw imagery of the landing location of interest.

Figure 9:
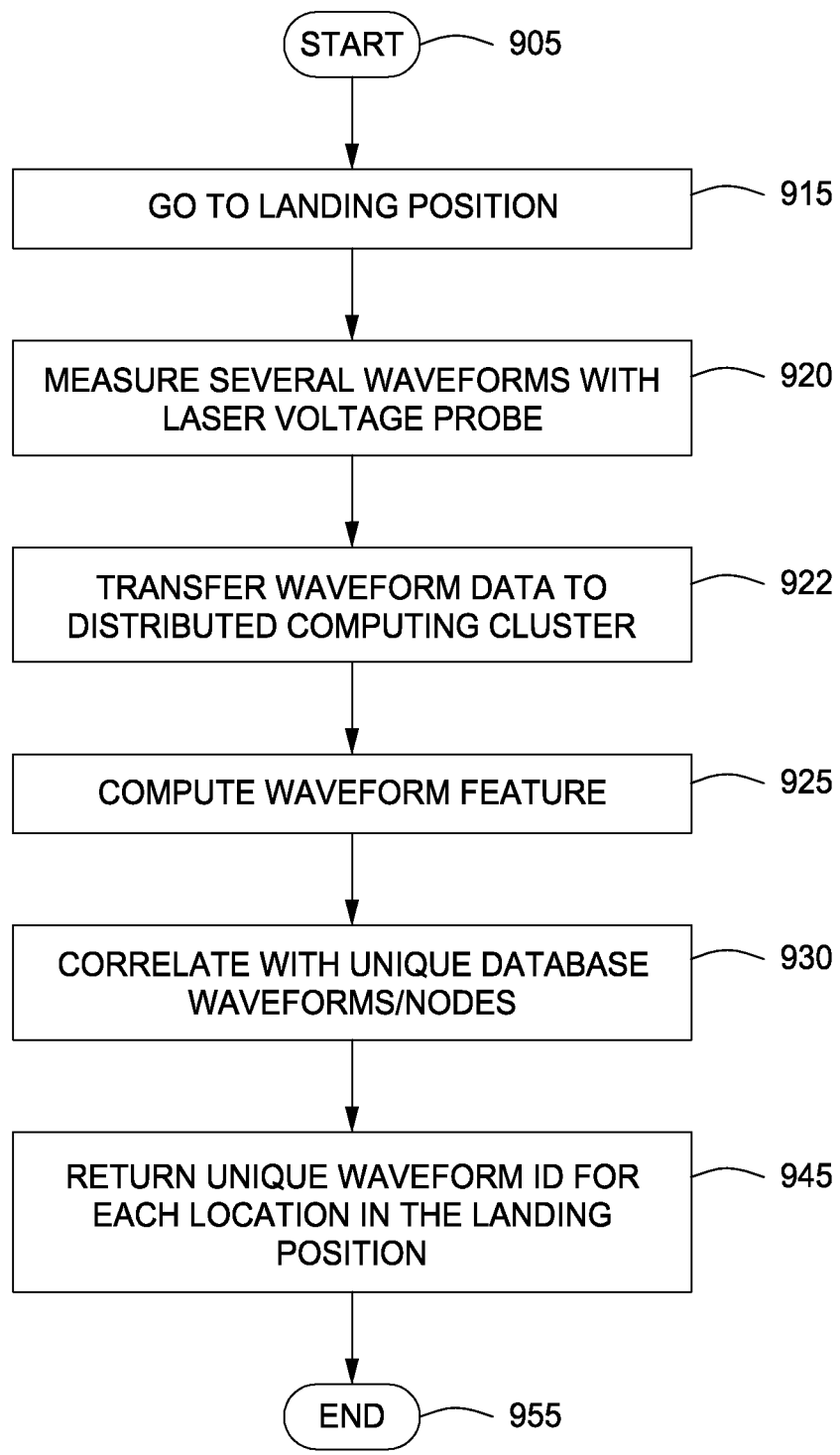
FIG. 9 depicts a flow diagram of a method for identifying logic cell interconnects in accordance with at least one embodiment of the invention.

FIG. 9 depicts a method 900 for extracting interconnects in accordance with exemplary embodiments of the present invention. The method 900 is an exemplary implementation of the steps performed by the super-resolution reconstruction module 630 shown in FIG. 6. Method 900 is used to identify electrical connections between logic cells with the assistance of a distributed computing cluster that may be composed of a multitude of GPUs (graphical processing units), CPUs (central processing units), FPGAs (field programmable gate arrays), or some combination thereof. The waveform structure is essentially unchanged within each node. The method 900 begins at step 905 and proceeds to step 915, where a landing position is established, i.e. IC stage coordinate. Then, at step 920, the method 900 measures several clean waveforms from the device under test 102, created by averaging several noisy waveforms, corresponding to one or more test vector sets. Next, the method transfers those waveforms to the distributed computing cluster in step 925. In step 925, the distributed computing cluster computes a feature vector from the content of the waveform, and then in step 930 the correlation score is computed between each waveform and those unique waveforms with similar features stored in the database. If the correlation is above a given threshold, the new waveform is said to connect to the stored node ID and is assigned to that node ID, and the database waveform for the unique node is updated to reflect the newly joined waveform. If the correlation is below a threshold, the waveform is used to create a new node with new unique node ID. Finally, the node ID for each waveform and location in the field of view is associated with each active region in the landing location and uploaded to the database in step 945. The algorithm concludes in step 955.

Figure 10:
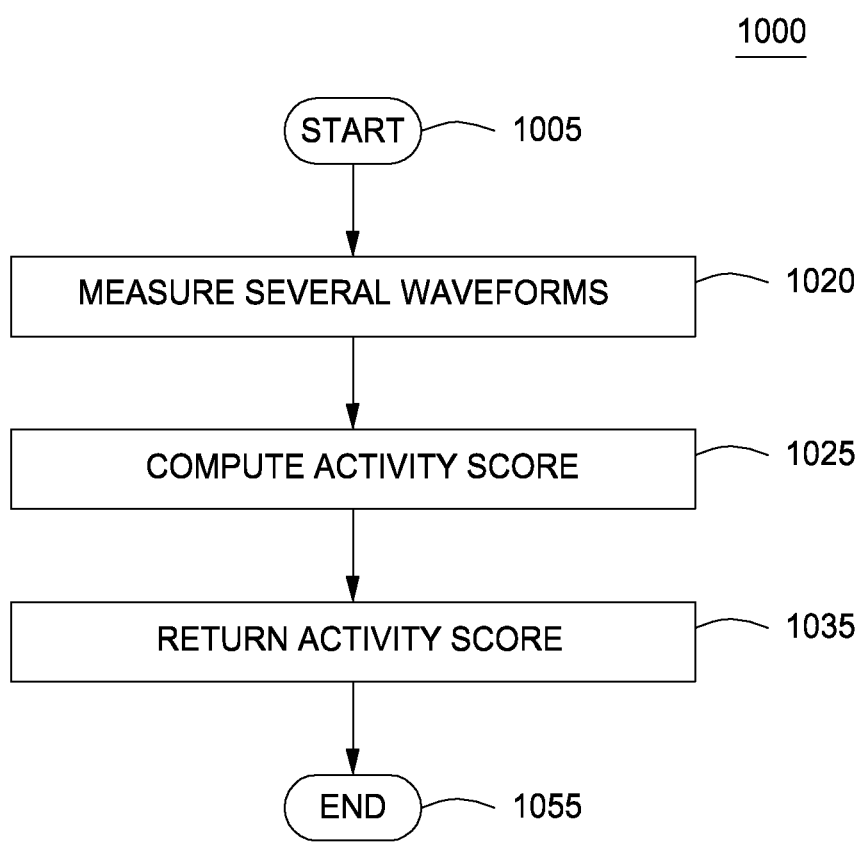
FIG. 10 depicts a flow diagram of a method for identifying activity in logic cells in accordance with at least one embodiment of the invention.

FIG. 10 depicts a flow diagram for a method 1000 for detecting activity in accordance with exemplary embodiments of the present invention. The method 1000 describes an exemplary embodiment of step 755 in method 700. The method 1000 is used to identify the presence of electronic waveforms within an IC without the need for longer averaging to measure the waveform. The algorithm begins at step 1005 while the device 102 is operated with test vectors. Several Laser Voltage Probed (LVP) signals, i.e. noisy waveforms, are acquired using a standard AC coupled photodetector and RF amplifier assembly in step 1020. The activity detector algorithm computes an activity score A in step 1025. According to an exemplary embodiment, A is computed using the following equation:

$$A(x) = (N_{records} - 1) \frac{\sum_{n=1}^{N_{records}} w_n^T w_\mu}{\sum_{n=1}^{N_{records}} w_n^T w_n - w_n^T w_\mu}$$

The score is computed by summing the dot product (correlation) of each individual with the waveform with the average and dividing by the sum of the difference of the self-correlation and the correlation with the mean for all waveforms. In this way, we can determine with only a few measurements whether there exists a waveform at all to be measured. The method 1000 then returns the activity score in step 1035 and ends at 1055.

Figure 11:
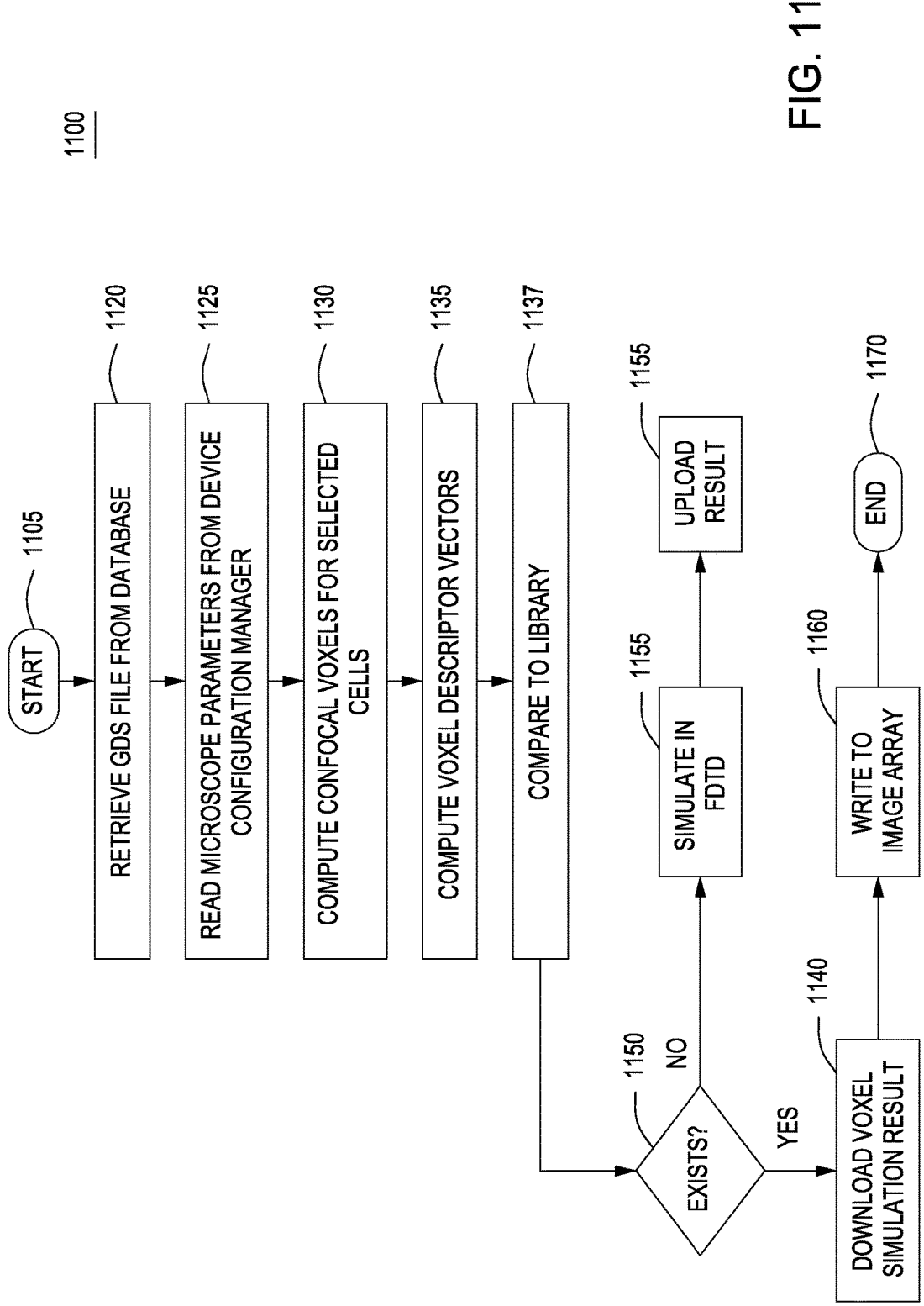
FIG. 11 depicts a flow diagram of a method for rapidly simulating object reflectivity using an electromagnetic simulator in accordance with at least one embodiment of the invention.

FIG. 11 depicts a flow diagram of a method 1100 in accordance with exemplary embodiments of the present invention. The Rapid Electromagnetic Simulator 690 implements the method 1100. The method 1100 takes as input the GDS layout information contained in the database 130 and simulates how such a layout will appear in the microscope. The method has two main components: first a gallery of simulated features is created using only unique voxels contained in the GDS library. Gallery creation may happen while GDS files are simulated. The method begins at step 1105 and proceeds to step 1120, wherein the algorithm reads one or more GDS files from the database 130. The coordinate scaling and units of the GDS information are also read. Microscope configuration information is used to compute the size of the voxel, or confocal volume of the laser scanning microscope, and voxel spacing. GDS file is then partitioned into a set of non-overlapping voxels in step 1135. A descriptor, which may be a binary, 1D array, is computed for each individual voxel. The voxel descriptors are then clustered and representatives from each unique voxel are held in memory. Unique voxel descriptors are compared to those found in the database in step 1137 using any manner of feature vector comparison such as dot products, or NOR operations. If the voxel is not found to already exist at step 1150, the voxel is transferred into a 3D array of points containing optical dielectric parameters and then simulated using a finite difference time-domain (FDTD) or similar Maxwell's equation solver in step 1155, where the initial beam is assumed to be a focused beam with parameters consistent with the voxel size. The simulated result is then uploaded to the database 130 in step 1155 and a relational identifier is created in the table of voxels that can be used to later retrieve the image. If the voxel is found to exist in the library at step 1150, rather than simulate it, the method 1100 simply downloads the simulation result in step 1140 from the database and writes the result to that portion of the image simulation in step 1160. This process may be repeated for every cell in the library and completes at step 1170. The advantage of this procedure for simulating a system is that speed is increased due to the high degree of symmetry contained in GDS files, while accuracy is maintained with the accurate Maxwell's solvers, which are typically too slow to simulate large structures on their own. In this way, many large structures can be simulated quickly and accurately.

The various embodiments of the invention described above can be used in various commercial applications such as: to verify netlists generated using the techniques described herein, testing of integrated circuits to ensure design accuracy or optimization, and reverse engineering of integrated circuits to create a netlist from an unknown integrated circuit.

While the foregoing is directed to embodiments of the present invention, other and further embodiments of the invention may be devised without departing from the basic scope thereof, and the scope thereof is determined by the claims that follow.

The invention claimed is:

1. An apparatus for scanning an integrated circuit comprising:
    a plurality of laser scanning microscopes comprising different wavelengths of laser light and configurable to operate using different scanning patterns and laser modulation frequencies, configured to pump a same field of view of at least a portion of the integrated circuit with photocarriers having at least one different wavelength, scanning pattern or modulation frequency to cause changes in electrical characteristics of at least the portion of the integrated circuit and generate a plurality of multi-dimensional images of the electrical characteristics of the integrated circuit; and
    a data processor, coupled to the laser scanning microscope, for processing the plurality of multi-dimensional images, the data processor comprising:
    a netlist extractor (NE) that, using the plurality of multi-dimensional images, produces one or more netlists defining structures of the integrated circuit.

2. The apparatus of claim 1 wherein the plurality of images form a hyper-dimensional representation of the integrated circuit under test.

3. The apparatus of claim 1 wherein the NE uses multi-modal processing of the plurality of images and defines unique features based on the plurality of images.

4. The apparatus of claim 1 wherein the data processor simultaneously interacts with a database, distributed computing cluster and the plurality of microscopes and the database comprises library information, data and analysis results.

5. The apparatus of claim 1 wherein the laser scanning microscope utilizes a pump/probe technique to generate the plurality of images.

6. The apparatus of claim 5 wherein the pump/probe technique uses a wavefront distortion mechanism to create a structured pump laser for injecting charge carries into the integrated circuit under test in a predetermined pattern to generate a plurality of charge flow images.

7. The apparatus of claim 6, further comprising:
    a phase-resolving detector for collecting a charge flow signal, wherein a unique color is assigned to each phase of the signal and each phase is plotted as a phase image.

8. The apparatus of claim 6, wherein a super-resolved image of the integrated circuit under test is constructed using the plurality of charge flow images.

9. The apparatus of claim 1, wherein the plurality of laser scanning microscopes comprise a pump laser to inject carriers into portions of the integrated circuit under test to suppress activity and a probe laser for detecting the pump laser at other connected transistors in the integrated circuit under test.

10. The apparatus of claim 9, wherein pump and probe lasers are sub-picosecond, ultrafast lasers.

11. The apparatus of claim 9, wherein a delay between the pump and probe lasers is adjusted for creating different images based on the delay.

12. The apparatus of claim 9, wherein the pump laser is further used to suppress an output of a logic cell in the integrated circuit under test, and the probe laser is used to observe an effect of the suppression elsewhere in the integrated circuit under test.

13. The apparatus of claim 1 wherein plurality of images may be generated by at least two of AC or DC reflectivity scans, AC or DC absorption scans, LIVA scans, OBIC scans, single point scans while varying test vectors, charge flow images, ultrafast charge flow images, time-delayed ultrafast charge flow images, activity images, waveform images, or phase images scans at a plurality of laser wavelengths.

14. The apparatus of claim 1 further comprising an AC-coupled RF detector, coupled to the data processor, for measuring RF components of reflectivity signals in a probe laser of the plurality of laser scanning microscopes, in selected frequency ranges.

15. The apparatus of claim 14 wherein the data processor determines a presence and strength of activity at a portion of the integrated circuit under test using correlations between a set of RF reflectivity measurements and statistical mean of a set of waveforms, and the data processor generates an activity map based on the determined presence and strength of activity.

16. The apparatus of claim 15 wherein the activity map is used to determine interconnections between elements of the integrated circuit under test.

17. The apparatus of claim 16, wherein the activity map is stored in a database and is used for determining where to collect RF waveform data from the integrated circuit under test, the RF waveform data is collected and stored in the database, and unique waveforms are identified and used to identify electrical connections between regions of the integrated circuit under test.

18. A method for scanning an integrated circuit comprising:
    using a plurality of laser scanning microscopes, pumping a same field of view of the integrated circuit with photocarriers having at least one different wavelength, scanning pattern or modulation frequency to cause changes in electrical characteristics of at least a portion of the integrated circuit and generate a plurality of multi-dimensional images of the electrical characteristics of the integrated circuit; and
    processing the plurality of multi-dimensional images to produce a netlist defining a structure of the integrated circuit.

19. The method of claim 18 wherein the plurality of images form a hyper-dimensional representation of the integrated circuit under test.

20. The method of claim 18 wherein multimodal processing of the plurality of images is used to create hyper-dimensional descriptors for regions of the integrated circuit under test.

21. The method of claim 20 further comprising:
    detecting objects from a library of objects using the multimodal processing;
    selecting one or more areas of the integrated circuit under test to measure activity; and
    collecting waveform data from the one or more areas with activity.

22. The method of claim 21, further comprising:
constructing additional dimensions for the multimodal processing using the collected waveform data and their corresponding areas;
correlating waveform data using a distributed computing cluster; and
identifying unique nodes in the integrated circuit under test, the unique nodes indicating electrically connected portions of the integrated circuit under test.

23. The method of claim 22, further comprising:
associating the unique nodes with the collected waveform data through a statistical average of all waveforms with correlations above a predetermined threshold amount.

24. The method of claim 23, further comprising:
identifying node assignments of new waveforms and their associated coordinates on the integrated circuit under test using the correlation waveform data and statistically averaged waveforms.

25. The method of claim 24, further comprising:
constructing a netlist, using the unique nodes, their locations and library objects, in a format of at least one of SPICE or Verilog.

* * * * *